United States Patent
Klofta et al.

(10) Patent No.: US 6,238,682 B1
(45) Date of Patent: *May 29, 2001

(54) ANHYDROUS SKIN LOTIONS HAVING ANTIMICROBIAL COMPONENTS FOR APPLICATION TO TISSUE PAPER PRODUCTS WHICH MITIGATE THE POTENTIAL FOR SKIN IRRITATION

(75) Inventors: Thomas James Klofta; Mark John Steinhardt, both of Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/041,231

(22) Filed: Mar. 12, 1998

Related U.S. Application Data

(63) Continuation of application No. 08/658,342, filed on Jun. 5, 1996, now Pat. No. 5,830,487, which is a continuation of application No. 08/398,727, filed on Mar. 6, 1995, now Pat. No. 5,525,345, which is a continuation of application No. 08/165,767, filed on Dec. 13, 1993, now abandoned.

(51) Int. Cl.⁷ .................................................. A01N 25/34
(52) U.S. Cl. .................. 424/402; 424/70.12; 424/78.03; 424/401; 424/404; 424/405; 514/844; 514/937; 514/943; 514/944
(58) Field of Search .................. 424/401, 70.12, 424/405, 78.3, 404; 510/235, 426; 514/844, 937, 943, 944

(56) References Cited

U.S. PATENT DOCUMENTS

| | | | |
|---|---|---|---|
| 3,138,533 | 6/1964 | Heim et al. | 167/84 |
| 3,227,614 | 1/1966 | Scheuer | 167/84 |
| 3,305,392 | 2/1967 | Britt | 117/154 |
| 3,814,096 | 6/1974 | Weiss et al. | 128/260 |

(List continued on next page.)

FOREIGN PATENT DOCUMENTS

| | | | |
|---|---|---|---|
| 850719 | 5/1977 | (BE) . | |
| 932936 | 9/1973 | (CA) . | |
| 3924898 A1 | 1/1991 | (DE) | D21H/17/71 |

(List continued on next page.)

OTHER PUBLICATIONS

"Virucidal Activity of Organic Acids", G. Poli, P.A. Biondi, F. Uberti, W. Ponti, A. Belsari, & C. Cantoni, *Food Chemistry*, (1979) 4(4), pp. 251–258.

(List continued on next page.)

Primary Examiner—Jose' G. Dees
Assistant Examiner—Kathryne E. Shelborne
(74) Attorney, Agent, or Firm—Julia A. Glazer; Larry L. Huston; Tara M. Rosnell

(57) ABSTRACT

An anhydrous lotion composition for killing viruses and bacteria in addition to imparting a soft, lubricious, lotion-like feel when applied to tissue paper and tissue paper treated with such lotion compositions are disclosed. The antiviral action of the lotion is due to the addition of an organic acid such as citric acid or salicylic acid. The antibacterial action is due to the addition of antibacterial agents such as TRICLOSAN®. The solubilization of the antiviral and antibacterial agents within the lotion matrix is aided by the addition of hydrophilic solvents and hydrophilic surfactants. The lubricious lotions also contain a plastic or fluid skin conditioning agent such as petrolatum, an optional immobilizing agent such as a fatty alcohol or fatty acid to immobilize the skin conditioning agent on the surface of the tissue paper web and a hydrophilic surfactant to improve wettability when applied to toilet tissue. Because less lotion is required to impart the desired soft, lotion-like feel benefits, detrimental effects on the tensile strength and caliper of the lotioned paper are minimized or avoided. The anhydrous nature of the lotions also aids in the maintenance of such physical properties as tensile and caliper.

28 Claims, 2 Drawing Sheets

U.S. PATENT DOCUMENTS

| | | | |
|---|---|---|---|
| 3,821,068 | 6/1974 | Shaw | 162/111 |
| 3,867,300 | 2/1975 | Karabinos et al. | 252/106 |
| 4,112,167 | 9/1978 | Dake et al. | 428/154 |
| 4,355,021 | 10/1982 | Mahl et al. | 424/28 |
| 4,481,243 | 11/1984 | Allen | 428/154 |
| 4,513,051 | 4/1985 | Lavash | 428/212 |
| 4,613,447 | 9/1986 | Hara et al. | 252/91 |
| 4,738,847 | 4/1988 | Rothe et al. | 424/443 |
| 4,764,418 | 8/1988 | Kuenn et al. | 428/284 |
| 4,767,788 | 8/1988 | Diana | 514/574 |
| 4,824,689 | 4/1989 | Kuenn et al. | 427/2 |
| 4,828,912 | 5/1989 | Hossain et al. | 428/289 |
| 4,897,304 | 1/1990 | Hossain et al. | 428/289 |
| 4,943,350 | 7/1990 | Bogart et al. | 162/158 |
| 4,975,217 | 12/1990 | Brown-Skrobot et al. | 252/107 |
| 5,004,636 | 4/1991 | Parris | 428/43 |
| 5,059,282 | 10/1991 | Ampulski et al. | 162/111 |
| 5,246,546 | 9/1993 | Ampulski | 162/112 |
| 5,525,345 | 6/1996 | Warner et al. | 424/402 |
| 5,525,346 | 6/1996 | Hartung et al. | 424/402 |
| 5,624,676 | 4/1997 | Mackey et al. | 424/414 |
| 5,648,083 | 7/1997 | Blieszner | 424/402 |
| 5,652,049 | 7/1997 | Suzuki | 442/387 |
| 5,665,426 | 9/1997 | Krzysik et al. | 427/211 |
| 5,674,513 | 10/1997 | Snyder, Jr. et al. | 424/404 |
| 5,681,852 * | 10/1997 | Bissett | 514/556 |
| 5,686,088 | 11/1997 | Mitra et al. | 424/404 |
| 5,686,089 | 11/1997 | Mitra et al. | 424/405 |
| 5,697,577 | 12/1997 | Ogden | 242/598.6 |
| 5,705,164 | 1/1998 | Mackey et al. | 424/400 |
| 5,720,966 | 2/1998 | Ostendorf | 424/402 |
| 5,762,948 * | 6/1998 | Blackburn et al. | 424/404 |
| 5,830,487 * | 11/1998 | Klofta et al. | 424/402 |
| 5,871,763 | 2/1999 | Luu et al. | 424/402 |

FOREIGN PATENT DOCUMENTS

| | | | |
|---|---|---|---|
| 4000920 A1 | 7/1991 | (DE) | D06M/23/12 |
| 0008121 A1 | 2/1980 | (EP) | A01N/37/04 |
| 0049354 | 4/1982 | (EP) | A61K/31/19 |
| 2 538 238 | 6/1984 | (FR) | A47K/7/03 |
| 1424692 | 2/1976 | (GB) | D21H/5/22 |
| 2 103 089 | 2/1983 | (GB) | A61H/31/19 |
| 2143249 | 2/1985 | (GB) | C11D/7/24 |
| 7102420 | 8/1972 | (NL) | D21H/5/22 |
| WO 95/16824 | 6/1995 | (WO) | D21H/17/14 |
| WO 95/35411 | 12/1995 | (WO) | D21H/21/24 |
| WO 95/35412 | 12/1995 | (WO) | D21H/21/24 |
| WO 97/16066 | 5/1997 | (WO) | A01N/25/04 |
| WO 97/30217 | 8/1997 | (WO) | D21H/17/07 |
| 9005876 | 5/1991 | (ZA) . | |
| 970823 | 1/1997 | (ZA) . | |

OTHER PUBLICATIONS

"Inactivation of Influenza and Other Viruses by a Mixture of Virucidal Compounds", J.S. Oxford, C.W. Potter, C. McLaren & W. Hardy, *Applied Microbiology*, Apr. 1971, vol. 21, No. 4, pp. 606–610.

"Recurrent Urinary Tract Infections In Women: Prevention By Topical Application of Antimicrobial Ointment To Urethral Meatus" Ralph R. Landes, Irving Melnick and Allan A. Hoffman *The Journal of Urology*, vol. 104, Nov. pp. 749–750.

"Antibacterial Perineal Washing For Prevention of Recurrent Urinary Tract Infections" A.S. Cass, and G.W. Ireland *Urology*, May 1985, vol. XXV, No. 5, pp. 492–494.

* cited by examiner

ANHYDROUS SKIN LOTIONS HAVING ANTIMICROBIAL COMPONENTS FOR APPLICATION TO TISSUE PAPER PRODUCTS WHICH MITIGATE THE POTENTIAL FOR SKIN IRRITATION

This application claims priority to and is a continuation of commonly assigned U.S. application Ser. No. 08/658,342 filed Jun. 5, 1996 (U.S. Pat. No. 5,830,487 iss. Nov. 3, 1998), which is a continuation of commonly assigned application Ser. No. 08/165,767 filed Dec. 13, 1993, abandoned and a continuation upon filing commonly assigned application Ser. No. 08/398,727, filed Mar. 6, 1995 (U.S. Pat. No. 5,525,345 iss. Jun. 11, 1996).

TECHNICAL FIELD

This application relates to anhydrous skin lotion compositions having antimicrobial components wherein the skin lotions impart a soft, lubricious feel to tissue paper and wherein the lotion compositions have the ability to kill certain strains of viruses and bacteria which come into contact with the lotioned paper. In addition to having antimicrobial components, these anhydrous lotions tend to be mild to the skin thus mitigating the potential for skin irritation. The absence of water in these lotions leads to advantages in maintaining such paper physical properties as tensile and caliper. This application further relates to tissue paper treated with such antimicrobial anhydrous lotion compositions.

BACKGROUND OF THE INVENTION

Whether it be a household, workplace, educational facility or any other location where people tend to gather, preventing the spread of germs is a difficult but yet desirable task. For instance, it is well documented that many hours of productive work are lost due to individuals becoming infected with the common cold or influenza virus. In addition, many dollars are spent annually on medicines to temper the ailments associated with the common cold and influenza. To prevent or slow the spread of germs within these previously noted areas, antimicrobial sprays, liquid cleaning products, and soaps exist for general sanitization and disinfection. Sprays are typically used to clean in and around sinks, bath tubs, showers and toilets. Liquid hard surface cleaners with antimicrobial components are now available for cleaning floors, countertops and other hard surfaces. In addition, a variety of antimicrobial soaps can be purchased for skin and body cleansing.

When one suffers from the common cold or influenza virus, one's mucus is the source of a very high concentration of viruses. After the mucus is blown into a facial tissue, the virus within the mucus has the potential to infect other individuals coming into contact with it. Transfer of this mucus on the tissue to another individual will likely be through accidental or unintentional contact.

As an example of a possible transfer scenario, consider a cold sufferer who accidentally leaves a mucus infected facial tissue on a hard surface of some type. This hard surface might be a kitchen countertop, a bathroom vanity surface, an office desk or some other piece of furniture. Another family member or colleague may accidentally come into contact with the infected mucus after picking up the tissue to throw it away. After coming into such contact with the mucus on the tissue, it is very possible for that individual to become infected with the viral condition (i.e., common cold, influenza) especially if the infected mucus comes into contact with that individual's mucosal membranes.

Another transmission scenario is through the disposal of the facial tissues contaminated with the virus containing mucus. After a household waste basket becomes filled with trash containing a high concentration of infected tissues, it obviously needs to be disposed of in some manner. During this transfer of the household trash into another larger disposal unit, the individual transferring the trash may come into contact with the contaminated tissue. Once again, this individual is at a higher risk for contracting the virus.

Many other potential modes of virus transmission are possible after the facial tissue has become infected with the mucus. To reduce the probability of cold and influenza transmission, the tissue coated with the antiviral anhydrous lotion described herein will kill some strains of both rhinovirus and influenza. By killing these viruses within the tissue, there is intervention in transmission of these viruses that cause the common cold and influenza.

Kimberly-Clark's AVERT facial tissue product of several years back purported to contain effective germ killers, but the anionic surfactant in the germ killing vehicle was likely too irritating to the skin. As is well known, cold and influenza sufferers typically have sore and irritated skin regions associated with the nose and lips. After blowing the aqueous mucus into the tissue, the anionic surfactant becomes easily dissolved and partially transferred to the irritated skin regions. These sensitive skin regions are more prone to irritation by anionic surfactants.

As noted, the irritation, inflammation and redness around the nose and lips can have several causes. A prime one is, of course, the sheer necessity of frequently blowing one's nose into the tissue, and wiping the resultant nasal discharge from the nose and surrounding area. The degree of irritation and inflammation caused by such blowing and wiping is directly proportional to: (1) the surface roughness of the tissue used; (2) the number of times the nose and its surrounding areas are in contact with the tissue; and (3) the irritation potential of any additives applied to the tissue paper. It is thus imperative to use ingredients within the antiviral lotion that are as mild as possible. In fact, it is more desirable to use ingredients that might provide a skin benefit.

In addition to the adverse skin reactions in AVERT, there was very little probability for dry transfer of the antiviral formulations to the skin. This was partly due to the addition of the AVERT antiviral composition to a third ply of tissue which was then sandwiched between two outside plies. In addition, the AVERT antiviral composition was made up of crystalline solids. Thus, after pulling out a tissue from the dispensing box, the probability of transferring the antiviral components to the fingers was low. Whereas, in the present invention if the lotion is applied to the outside plies of the tissue, the lotion can be readily transferred either to the skin or to inanimate objects by simply applying pressure between the lotioned tissue and the object being touched. Thus, the probability for skin or inanimate surface transfer is high, making it possible to kill viruses on animate and inanimate objects. The lotion of this invention may also be applied between the tissue plies.

In addition the present invention may also be applied to toilet tissue. Cleansing the skin in the perineal regions is a personal hygiene problem not always easily solved. Of course, the common procedure of washing the skin with soap and water works well, but at times these may either be unavailable or inconvenient to use. While soap and water could be used to clean the perianal region after defecation for example, such a procedure would be extremely burdensome.

The perianal skin is marked by the presence of fine folds and wrinkles (sulci) and by hair follicles, both of which make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content. It is malaodorous and generally dehydrated. These characteristics increase the likelihood of perianal disorders and cause personal discomfort (e.g., itiching, irritation, chafing, etc.) Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptitis, or the like, the importance of adequate perianal cleansing takes on heightened significance. Perianal disorders are usually characterized by opening in the skin through which the bacteria and viruses in the residual fecal matter can readily enter. Those people afflicted with anal disorders must, therefore, achieve a high degree of perianal cleansing after defecation or risk the likely result that their disorder will be aggravated by the bacteria and viruses remaining on the skin.

At the same time that anal disorder sufferers face more severe consequences from insufficient post defecation cleaning, they also have greater difficulty in achieving a satisfactory level of soil removal. Anal disorders generally render the perianal region extremely sensitive and attempts to remove fecal matter from this region by wiping with normal wiping pressure can cause pain and further irritate the skin. Attempts to improve soil removal by increasing the wiping pressure can result in intense pain. Conversely, attempts to minimize discomfort by reducing the wiping pressure result in an increased amount of residual fecal matter left on the skin.

Conventional toilet tissue products used for anal cleaning are essentially dry, high density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, thus causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, itching, and infection.

Hence, the irritation and inflammation potentially caused by the use of tissue products is a common drawback experienced by users of both toilet tissue and facial tissue.

It is thought that the present invention may also be useful in reducing the incidence of recurrent urinary tract infections, a problem which tends to plague women more commonly than men.

As the lotions of this invention are substantially anhydrous, they will not evaporate upon contact with the skin surface. Thus, in comparison to non-anhydrous lotions, the substantially anhydrous lotions of this invention provide more oppportunity for the lotion to be retained on the skin thereby providing a more lasting benefit to the skin surface.

Additionally, subsequent cleanings using the tissue paper of this invention tend to be more efficient. For instance, with toilet tissue, during the first use of the tissue, lotion is transferred from the tissue to the skin and hair in the perianal area. A lubricious layer, which includes surface tension-reducing surfactants, is created on the skin. Fecal matter which is subsequently deposited in this area, is more easily removed as a result of the lubricious layer. Hence, cleaning this area tends to become easier.

Accordingly, it would be desirable to provide lotioned tissue products that: (1) kill deleterious viruses within the tissue such as rhinovirus and influenza viruses; (2) that kill deleterious bacteria in the tissue such as *Escherichia coli* and Staphylococcus Saprophyticus (3) that contain antibacterial and antiviral components which can reduce the risk of bacterial and viral related perineal disorders; (4) contain antibacterial components which can reduce the risk of recurrent urinary tract infections (5) contain an antiviral and antibacterial anhydrous lotion that can be transferred to the skin or inanimate objects for possible kill of deleterious bacteria and viruses coming into contact with the lotioned skin or inanimate regions; (6) do not adversely affect the tensile strength, absorbency and caliper of the product; (7) are mild to the skin; (8) possess a soft and lubricious feel; (9) provide skin benefits associated with alpha and beta hydroxy acids; (10) contain an anhydrous lotion which limits lotion diffusion and aids in the maintenance of such physical properties as tensile and caliper; (11) optionally contain a natural oil such as eucalyptol, menthol, thymol, camphor, lemon oil, methyl salicylate, garlic oil and mixtures thereof; and (12) do not require special wrapping or barrier materials for packaging.

SUMMARY OF THE INVENTION

The present invention relates to a tissue paper having a lotion composition wherein the lotion composition comprises:

(A) at least one antimicrobial;
(B) at least one hydrophilic solvent;
(C) at least one skin conditioning agent; and
(D) at least one hydrophilic surfactant.

The lotion composition, which is preferably substantially water free, is generally applied in an amount ranging from about 2% to about 40% by weight of the dried tissue paper. At 20° C., the lotion composition is preferably a semi-solid or solid. The antimicrobial may be selected from the group consisting of antivirals, antibacterials and mixtures thereof. The antiviral is preferably an organic acid(s) which comprises from about 1% to 60% of the lotion composition.

Optionally, an inorganic acid may be added in conjunction with the organic acid to adjust pH. The optional inorganic acid may comprise from about 0.1% to 5% of the lotion composition.

The antibacterial component of the lotion comprises from about 0.1% to 6% of the lotion composition. The hydrophilic solvent which comprises from about 5% to 60% of the lotion composition, preferably has from about 1 to 150 carbon atom(s) wherein the carbon atom(s) are either branched or straight chained, saturated or unsaturated, with or without ether linkages and contains from about 1 to 302 hydroxyl group(s).

The skin conditioning agent of the lotion composition is preferably substantially water free and has a plastic or fluid consistency at 20° C. The skin conditioning agent comprises from about 0.1% to 60% of the lotion composition. The nonionic surfactant which comprises from about 1% to 50% of the lotion composition preferably has an HLB value of at least about 4. The lotion composition may also optionally include an immobilizing agent which comprises from about 5% to 60 of the lotion composition. The immobilizing agent preferably has a melting point of at least about 25° C. Other optional components which may be added to the lotion composition include natural essential oils, vitamins, panthenol, camphor, thymol menthol, eucalyptol, geraniol, lemon oil, methyl salicylate, clove, alcohol, and mixtures thereof. These other optional components can comprise from about 0.1% to 20% of the lotion composition.

DETAILED DESCRIPTION OF THE INVENTION

Figure 1:
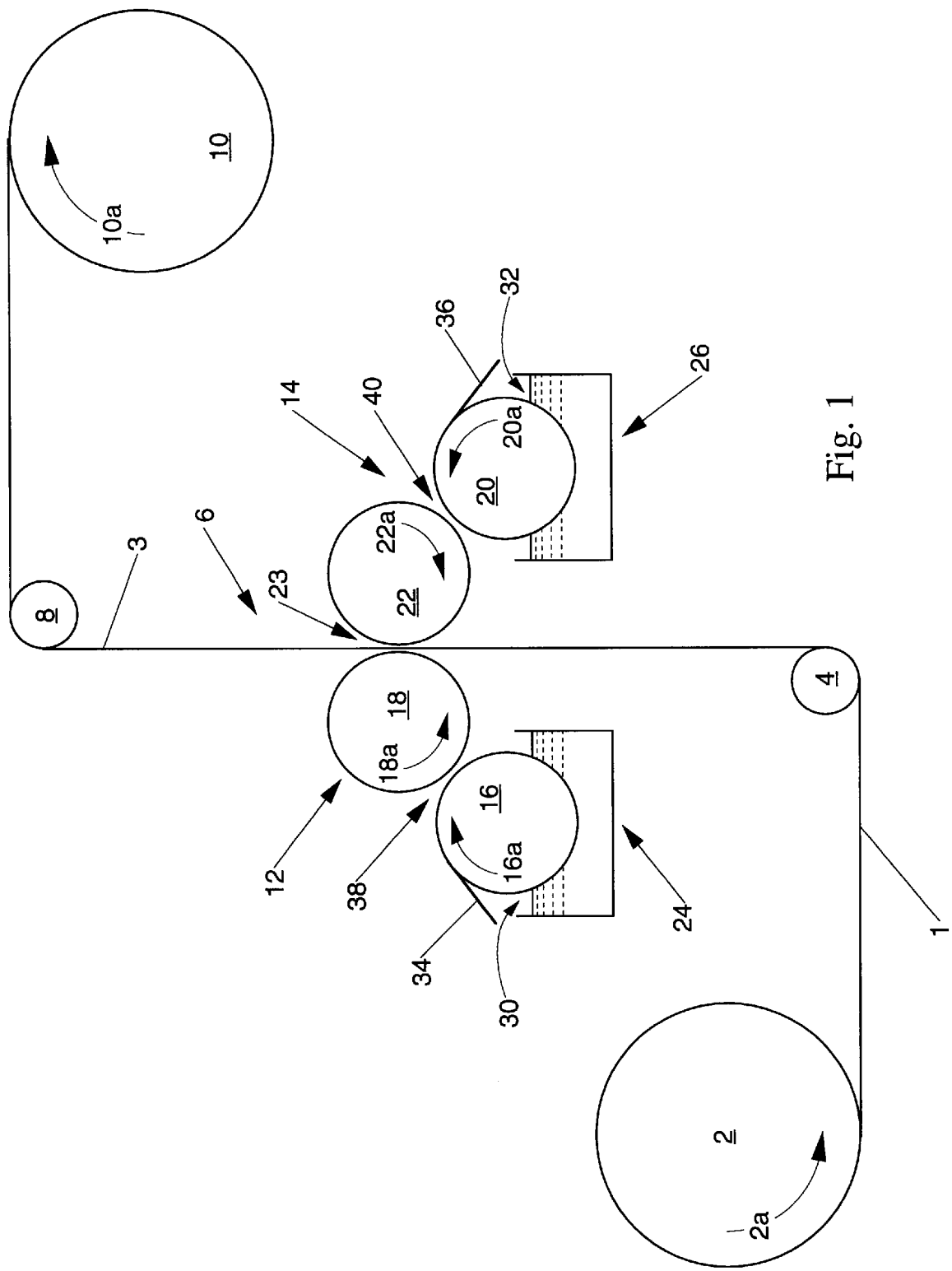
FIG. 1 is a schematic representation illustrating a preferred process for applying the lotion composition of the present invention to tissue paper webs.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

A. Tissue Papers

The present invention is useful with tissue paper in general, including but not limited to conventionally felt-pressed tissue paper; high bulk pattern densified tissue paper; and high bulk, uncompacted tissue paper. The tissue paper can be of a homogenous or multi-layered construction; and tissue paper products made therefrom can be of a single-ply or multi-ply construction. The tissue paper preferably has a basis weight of between about 10 g/m$^2$ and about 65 g/m$^2$, and density of about 0.6 g/cc or less. More preferably, the basis weight will be about 40 g/m$^2$ or less and the density will be about 0.3 g/cc or less. Most preferably, the density will be between about 0.04 g/cc and about 0.2 g/cc. See Column 13, lines 61–67, of U.S. Pat. No. 5,059,282 issued to Ampulski et al. on Oct. 22, 1991, and incorporated herein by reference which describes how the density of tissue paper is measured. (Unless otherwise specified, all amounts and weights relative to the paper are on a dry basis.)

Conventionally pressed tissue paper and methods for making such paper are well known in the art. Such paper is typically made by depositing a papermaking furnish on a foraminous forming wire, often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided from a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The tissue paper structures that are formed are referred to hereafter as conventional, pressed, tissue paper structures. Such sheets are considered to be compacted since the entire web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non-ornamental configuration or can be formed so as to provide an ornamental design(s) in the tissue paper. Preferred processes for making pattern densified tissue webs are disclosed in U.S. Pat. No. 3,301,746, issued to Sanford et al. on Jan. 31, 1967; U.S. Pat. No. 3,974,025, issued to Ayers on Aug. 10, 1976; U.S. Pat. No. 4,191,609, issued to Trokhan on Mar. 4, 1980; and U.S. Pat. No. 4,637,859, issued to Trokhan on Jan. 20, 1987; all of which are incorporated by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further dedensified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles that operate as the array of supports that facilitate the formation of the densified zones upon application of pressure. The pattern of knuckles constitutes the array of supports previously referred to. Suitable imprinting carrier fabrics are disclosed in U.S. Pat. No. 3,301,746, issued to Sanford et al. on Jan. 31, 1967; U.S. Pat. No. 3,821,068, issued to Salvucci et al. on May 21, 1974; U.S. Pat. No. 3,974,025, issued to Ayers on Aug. 10, 1976; U.S. Pat. No. 3,573,164, issued to Friedberg et al. on Mar. 30, 1971; U.S. Pat. No. 3,473,576, issued to Amneus on Oct. 21, 1969; U.S. Pat. No. 4,239,065, issued to Trokhan on Dec. 16, 1980; and U.S. Pat. No. 4,528,239, issued to Trokhan on Jul. 9, 1985, all of which are incorporated by reference.

Preferably, the furnish is first formed into a wet web on a foraminous forming carrier, such as a Fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally predried to a selected fiber consistency from about 40% to about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000, issued to Salvucci et al. on May 21, 1974 and U.S. Pat. No. 4,208,459, issued to Becker et al. on Jun. 17, 1980, both of which are incorporated by reference. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least about 80%, and creping the web. Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of about 25–50%, transferring the web to a thermal dryer such as a Yankee and creping the web. Overall, water is removed from the web by vacuum, mechanical pressing and thermal means. The resulting structure is strong and generally of singular density, but very low in bulk, absorbency and softness.

The papermaking fibers utilized for the present invention will normally include fibers derived from wood pulp. Other cellulosic fibrous pulp fibers, such as cotton linters, bagasse, etc., can be utilized and are intended to be within the scope of this invention. Synthetic fibers, such as rayon, polyethylene, polypropylene fibers, and MICROBAN®, a material manufactured by Microban Products Co. of Huntersville, N.C., can also be utilized in combination with natural cellulosic fibers. One exemplary polyethylene fiber that can be utilized is PULPEX®, available from Hercules, Inc. of Wilmington, Del.

Applicable wood pulps include chemical pulps, such as kraft, sulfite, and sulfate pulps, as well as mechanical pulps including, for example, groundwood, thermomechanical pulp and chemically modified thermomechanical pulp. Chemical pulps, however, are preferred since they impart a superior tactile sense of softness to tissue sheets made therefrom. Pulps derived from both deciduous trees (hereafter, also referred to as "hardwood") and coniferous trees (hereafter, also referred to as "softwood") can be utilized. Also useful in the present invention are fibers derived from recycled paper, which can contain any or all of the above categories as well as other non-fibrous materials such as fillers and adhesives used to facilitate the original papermaking. Fillers comprising zinc oxide can be advantageous in the present invention due to the potential skin benefits derived from their use.

In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as toilet tissue, paper towels, facial tissues and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins have been found to be of particular utility. Suitable types of such resins are described in U.S. Pat. No. 3,700,623, issued to Keim on Oct. 24, 1972, and U.S. Pat. No. 3,772,076, issued to Keim, on Nov. 13, 1973, both of which are incorporated by reference. One commercial source of a useful polyamide-epichlorohydrin resin is Hercules, Inc. of Wilmington, Del., which markets such resins under the name of KYMENE® 557H.

Polyacrylamide resins have also been found to be of utility as wet strength resins. These resins are described in U.S. Pat. Nos. 3,556,932, issued to Coscia et al. on Jan. 19, 1971, and 3,556,933, issued to Williams et al. on Jan. 19, 1971, both of which are incorporated herein by reference. One commercial source of polyacrylamide resins is American Cyanamid Co. of Stamford, Conn., which markets one such resin under the name of PAREZ® 631 NC.

Still other water-soluble cationic resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as CALDAS 10 (manufactured by Japan Carlit) and COBOND 1000 (manufactured by National Starch and Chemical Company of Bridgewater, N.J.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the finished tissue paper product, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the tissue paper.

In general, suitable starch binders for the present invention are characterized by water solubility and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn", H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, of Bridgewater, N.J., that have previously been used as pulp furnish additives to increase wet and/or dry strength.

B. Lotion Composition

The lotion compositions of the present invention at 20° C., i.e. at ambient temperatures may be liquid, preferably semisolid or more preferably solid. The term "semisolid" refers to a lotion composition that has a rheology typical of pseudoplastic or plastic fluids. When no shear is applied, the lotion compositions can have the appearance of a semi-solid but can be made to flow as the shear rate is increased. This is due to the fact that, while the semisolid or solid lotion compositions contain primarily solid components, they may also include some minor liquid components.

The solid or semisolid consistency of the lotions at room temperature are due to the addition of high melting components such as those high melting organic acids having antiviral functionality; fatty alcohols; waxes; high molecular weight polyethylene glycols; polyoxyethylene mono-, di-, and tri-sorbitan alkylates; mono-, di-, and tri- sorbitan alkylates; and non-ionic ethoxylated surfactants. The high melting and higher molecular weight alkane fraction of petrolatum, which may be used as a skin conditioning agent in the present invention, can also contribute to raising the melting point of these lotions. These higher molecular weight components of petrolatum are typically high molecular weight waxy-type hydrocarbons.

The lotions of this invention which are solid or semisolid at ambient temperatures, do not have a tendency to flow and migrate into the interior of the tissue web to which they are applied. This means less lotion composition is required for imparting softness and lotion-like feel benefits. It also means there is less chance for debonding of the tissue paper that can potentially lead to decreases in tensile strength.

When applied to tissue paper, the lotion compositions of the present invention impart a soft, lubricious, lotion like feel to the user of the paper. This particular feel has also been characterized as "silky", "slick", "smooth", etc. Such a lubricious, lotion-like feel is particularly beneficial for those having more sensitive skin due to chronic conditions such as skin dryness or hemorrhoids, or due to more transient conditions such as colds or allergies. Transfer of the lotion to the skin provides the potential for skin benefits for those lotions containing alpha hydroxy and beta hydroxy acids. Additionally, an antimicrobial(s) such as an antiviral, an antibacterial or a combination of both within the lotion aids in the destruction of deleterious microorganisms such as viruses and bacteria. Lotion transfer to the skin can potentially protect those regions from viral and bacterial infections.

Finally, skin conditioning agents such as petrolatum, mineral oil, and dimethicones can form a protective layer on the skin and provide a moisturization or other skin conditioning benefit. In addition, the hydrophobic barrier formed on the skin by such actives as petrolatum, mineral oil, dimethicones and other similarly related molecules, may form a protective barrier on the skin and protect it from any chemicals present in either the lotion or the environment which could potentially irritate the skin.

The lotions of the present invention are substantially anhydrous. By substantially anhydrous it is meant that no water is intentionally added to these lotions. Typically, the ingredients used in the present invention contain about 5% or less water, preferably about 1.0% or less water, more preferably about 0.5% or less water, and most preferably about 0.1% or less water. The anhydrous nature of these lotions allows for more efficient dry transfer of the lotion to the skin. Intentional addition of water to the lotion would be detrimental to physical properties of the paper such as tensile and caliper. Water aids in the migration of the lotion throughout the tissue web. This leads to fiber debonding and less lotion concentrated at the surface of the paper. This leads to both tensile and caliper losses; thus, it is beneficial to maintain an anhydrous lotion state as described herein.

In addition, water tends to promote microbial growth; thus, it is advantageous to maintain an anhydrous lotion state as described herein. Also, since the absence of water promotes greater surface concentration of the lotion ingredients, the probability for more efficient dry skin transfer is enhanced if the lotion is applied to the consumer side of the outside plies of the tissue. The consumer side of the tissue, refers to the side of the tissue which comes into contact with the user. Of course, transfer to the skin is inhibited if the lotion is applied to the inside plies of the tissue.

The lotion compositions of the present invention comprise: (1) an antimicrobial(s); (2) a hydrophilic solvent(s); (3) a skin conditioning agent(s); (4) a hydrophilic surfactant (s); (5) an optional immobilizing agent(s); (6) an optional additive(s) such as natural essential oils, vitamins, aloe, panthenol, camphor, thymol, menthol, eucalyptol, geraniol, lemon oil, methyl salicylate, clove, alcohols.

1. Antimicrobial(s)

One of the key active ingredients in the lotion compositions of this invention is one or more antimicrobial(s). The antimicrobial(s) may be an antiviral(s), an antibacterial(s) or a combination of both.

Antiviral(s)

As used herein, an antiviral refers to something capable of killing viruses such as rhinovirus and influenza. Antivirals which may be added to the lotions of this invention include but are not limited to organic acids which have antiviral functionality. Organic acids useful with this invention include but are not limited to ascorbic acid and alpha hydroxy acids such as $C_1$–$C_{12}$ saturated and unsaturated, carboxylic acids possessing 1 to 4 carboxylic acid groups and having at least one hydroxyl group substituted on the $C_2$ alpha carbon with additional hydroxyl and other functionalities (i.e.; phenyl, amino, etc.) optionally bound along the carbon chain and aromatic ring(s). A non-inclusive list of alpha hydroxy acids which may be used includes: 2-hydroxyhexanoic acid, 2-hydroxyoctanoic acid, 2-hydroxydecanoic acid, 2-hydroxydodecanoic acid, 2-hydroxycaprylic acid, citric acid, tartaric acid, mandelic acid, malic acid, glycolic acid, lactic acid, gluconic acid, hydroxycaprylic acid, 2-hydroxypropionic acid, 2-hydroxybutanoic acid, 2-hydroxypentanoic acid, and mixtures thereof.

Other examples of organic acids useful with this invention include beta hydroxy acids such as $C_1$–$C_{12}$ saturated, unsaturated, and carboxylic acids possessing 1 to 4 carboxylic acid groups and having at least one hydroxyl group substituted on the $C_3$ beta carbon with additional hydroxyl and other functionalities (i.e.; phenyl, amino, hydroxyl, etc.) optionally bound along the carbon chain or aromatic ring(s). A non-inclusive list of beta hydroxy acids useful with this invention includes: 3-hydroxyhexanoic acid, 3-hydroxyoctanoic acid, 3-hydroxydecanoic acid, 3-hydroxydodecanoic acid, 3-hydroxycaprylic acid, salicylic acid, 3-hydroxybutanoic acid, 3-hydroxypentanoic acid, 3-hydroxypropionic acid, and mixtures thereof.

A non-inclusive list of other organic acids useful with this invention includes $C_1$–$C_{12}$ saturated, unsaturated, and aromatic carboxylic acids possessing 1 to 4 carboxylic acid groups with optional functional groups (i.e.; phenyl, amino, hydroxyl, etc.) substituted along the carbon chain or on the aromatic ring(s) such as propionic acid, hexanoic acid, octanoic acid, decanoic acid; $C_1$ to $C_{12}$ carboxylic acids possessing 1 to 4 carboxylic acid groups wherein a hydroxyl group(s) is substituted on carbon number(s) $C_4$ or above such as 4-hydroxyhexanoic acid, 5,6-dihydroxyhexanoic acid, 6-hydroxyhexanoic acid, 4-hydroxyoctanoic acid, 5-hydroxyoctanoic acid, 6-hydroxyoctanoic acid, 6,7,8-trihydroxyoctanoic acid, 8-hydroxyoctanoic acid, 4-hydroxydecanoic acid, 5-hydroxydecanoic acid, 6-hydroxydecanoic acid, 7-hydroxydecanoic acid, 8-hydroxydecanoic acid, 9-hydroxydecanoic acid, 10-hydroxydecanoic acid, 4-hydroxydodecanoic acid, 5-hydroxydodecanoic acid, 6-hydroxydodecanoic acid, 11-hydroxydodecanoic acid, and 12-hydroxydodecanoic acid; benzoic acid; phthalic acid; acetylsalicylic acid; dehydroacetic acid; sorbic acid; succinic acid; glutaric acid; adipic acid; sebacic acid; maleic acid; folic acid; acetic acid; ethylenediaminetetraacetic acid; glycolic acid; and mixtures thereof. Preferred organic acids include adipic acid, glutaric acid, succinic acid, lactic, and mixtures thereof. More preferred organic acids include acetylsalicylic acid, glycolic, and mixtures thereof. Most preferred organic acids are salicylic acid, citric acid, tartaric acid, ascorbic acid, and mixtures thereof.

Because of the pH lowering effect of these organic acids, viruses such as rhinovirus and influenza coming into contact with the acidified lotion on the tissue are killed. Some of the antiviral organic acids used in these lotions are from a class of acids termed alpha or beta hydroxy acids. In addition to their antiviral functionality, the skin benefits associated with these alpha or beta hydroxy acids are also provided to the consumer.

In addition to providing antiviral activity, some of these acids which are either within the alpha hydroxy class or beta hydroxy class of acids also function as skin exfoliants thus providing additional benefits to the skin. In addition to their antiviral properties, the use of the solid organic acids can contribute to lotion hardening and thus aid in inhibiting lotion migration within the fibrous paper substrate. The high melting points of the acids can also allow the lotion to solidify more quickly at the surface of the paper. This allows for more efficient use of the lotion and the surface confinement contributes to more effective virus kill as well as the potential for improved lotion feel. Acids with linear structures, such as octanoic acid, hexanoic acid, decanoic acid, adipic acid, succininc acid, and glutaric acid, are more crystalline and thus should lead to faster solidification of the lotion on the surface of the paper.

Inorganic acids may also be used in conjunction with the organic acids to adjust pH. A non-inclusive list of inorganic acids useful with this invention include hydrochloric acid, boric acid, and preferably phosphoric acid. The optional inorganic comprises from about 0.1% to 5% of the lotion composition.

Many theories exist as to how organic acids deactivate viruses such as rhinovirus and influenza. One possible mechanism for virus deactivation is the donation of protons from the acid to the amide nitrogen of one or all of the various proteins within the virus structure. This protonation leads to a net positive charge within the protein structure. This leads to repulsion between the protonated amide moieties of the high molecular weight protein molecules. This leads to denaturing of some or all of the protein structures within the virus. This denaturing or unfolding of the protein structure deactivates the virus.

Another potential mechanism for deactivation by the organic acids is through hydrolysis of the proteins and other molecules within the virus structure. This acid catalyzed hydrolysis most likely occurs through cleavage of the amide functionalities of the proteins making up the complex virus structure. This hydrolysis and breakage of the bonds of the proteins of the virus structure deactivates the virus and renders it ineffective in attacking healthy cells within the body. For enveloped viruses like influenza where the structure is surrounded by a lipid shell, the acid may also cause deactivation through hydrolysis of this lipid layer. In addition, some surfactants such as those of the ethoxylated alcohol type, can dissolve this lipid shell and render the virus inactive. The antiviral component(s) of the lotion comprises from about 1% to 60% of the lotion composition. Mixtures of the antivirals may also be used.

Antibacterial(s)

Antibacterials within the lotion can also aid in the lotion's ability to kill deleterious microorganisms such as *Escherichia coli* and Staphylococcus Saprophyticus. Antibacterials useful with this invention include but are not limited to:

Pyrithiones, especially sodium omadine and the zinc complex (ZPT)
OCTOPIROX®
Dimethyidimethylol Hydantoin (GLYDANT®)
Methylchloroisothiazolinone/methylisothiazolinone (KATHON CG®)
Sodium Sulfite
Sodium Bisulfite
Imidazolidinyl Urea (GERMALL 115®)
Diazolidinyl Urea (GERMALL II®)
Benzyl Alcohol
2-Bromo-2-nitropropane-1,3-diol (BRONOPOL®)
Formalin (formaldehyde)
Iodopropenyl Butylcarbamate (POLYPHASE P100®)
Chloroacetamide
Methanamine
Methyldibromonitrile Glutaronitrile (1,2-Dibromo-2,4-dicyanobutane or TEKTAMER)
Glutaraldehyde
5-bromo-5-nitro-1,3-dioxane (BRONIDOX®)
Phenethyl Alcohol
o-Phenylphenolsodium o-phenylphenol
Sodium Hydroxymethylglycinate (SUTTOCIDE A®)
Polymethoxy Bicyclic Oxazolidine (NUOSEPT C®)
Dimethoxane
Thiomersal
Dichlorobenzyl Alcohol
Captan
Chlorphenenesin
Dichlorophene
Chlorbutanol
Glyceryl Laurate
Halogenated Diphenyl Ethers
  2,4,4'-trichloro-2'-hydroxy-diphenyl ether (TRICLOSAN® or TCS)
  2,2'-dihydroxy-5,5'-dibromo-diphenyl ether
Phenolic Compounds
  Phenol
  2-Methyl Phenol
  3-Methyl Phenol
  4-Methyl Phenol
  4-Ethyl Phenol
  2,4-Dimethyl Phenol
  2,5-Dimethyl Phenol
  3,4-Dimethyl Phenol
  2,6-Dimethyl Phenol
  4-n-Propyl Phenol
  4-n-Butyl Phenol
  4-n-Amyl Phenol
  4-tert-Amyl Phenol
  4-n-Hexyl Phenol
  4-n-Heptyl Phenol
Mono and Poly-Alkyl and Aromatic Halophenols
  p-Chlorophenol
  Methyl p-Chlorophenol
  Ethyl p-Chlorophenol
  n-Propyl p-Chlorophenol
  n-Butyl p-Chlorophenol
  n-Amyl p-Chlorophenol
  sec-Amyl p-Chlorophenol
  n-Hexyl p-Chlorophenol
  Cyclohexyl p-Chlorophenol
  n-Heptyl p-Chlorophenol
  n-Octyl p-Chlorophenol
  o-Chlorophenol
  Methyl o-Chlorophenol
  Ethyl o-Chlorophenol
  n-Propyl o-Chlorophenol
  n-Butyl o-Chlorophenol
  n-Amyl o-Chlorophenol
  tert-Amyl o-Chlorophenol
  n-Hexyl o-Chlorophenol
  n-Heptyl o-Chlorophenol
  o-Benzyl p-Chlorophenol
  o-Benxyl-m-methyl p-Chlorophenol
  o-Benzyl-m, m-dimethyl p-Chlorophenol
  o-Phenylethyl p-Chlorophenol
  o-Phenylethyl-m-methyl p-Chlorophenol
  3-Methyl p-Chlorophenol
  3,5-Dimethyl p-Chlorophenol
  6-Ethyl-3-methyl p-Chlorophenol
  6-n-Propyl-3-methyl p-Chlorophenol
  6-iso-Propyl-3-methyl p-Chlorophenol
  2-Ethyl-3,5-dimethyl p-Chlorophenol
  6-sec-Butyl-3-methyl p-Chlorophenol
  2-iso-Propyl-3,5dimethyl p-Chlorophenol
  6-Diethylmethyl-3-methyl p-Chlorophenol
  6-iso-Propyl-2-ethyl-3-methyl p-Chlorophenol
  2-sec-Amyl-3,5-dimethyl p-Chlorophenol
  2-Diethylmethyl-3,5-dimethyl p-Chlorophenol
  6-sec-Octyl-3-methyl p-Chlorophenol
  p-Chloro-m-cresol
  p-Bromophenol
  Methyl p-Bromophenol
  Ethyl p-Bromophenol
  n-Propyl p-Bromophenol
  n-Butyl p-Bromophenol
  n-Amyl p-Bromophenol
  sec-Amyl p-Bromophenol
  n-Hexyl p-Bromophenol
  Cyclohexyl p-Bromophenol
  o-Bromophenol
  tert-Amyl o-Bromophenol
  n-Hexyl o-Bromophenol
  n-Propyl-m,m-Dimethyl o-Bromophenol
  2-Phenyl Phenol
  4-Chloro-2-methyl phenol
  4-Chloro-3-methyl phenol
  4-Chloro-3,5-dimethyl phenol
  2,4-Dichloro-3,5-dimethylphenol
  3,4,5,6-Terabromo-2-methylphenol
  5-Methyl-2-pentylphenol
  4-Isopropyl-3-methylphenol Para-chloro-meta-xylenol (PCMX)
Chlorothymol
Phenoxyethanol
Phenoxyisopropanol
5-Chloro-2-hydroxydiphenylmethane
Resorcinol and its Derivatives
　Resorcinol
　Methyl Resorcinol
　Ethyl Resorcinol
　n-Propyl Resorcinol
　n-Butyl Resorcinol
　n-Amyl Resorcinol
　n-Hexyl Resorcinol
　n-Heptyl Resorcinol
　n-Octyl Resorcinol
　n-Nonyl Resorcinol
　Phenyl Resorcinol
　Benzyl Resorcinol
　Phenylethyl Resorcinol
　Phenylpropyl Resorcinol
　p-Chlorobenzyl Resorcinol
　5-Chloro 2,4-Dihydroxydiphenyl Methane
　4'-Chloro 2,4-Dihydroxydiphenyl Methane
　5-Bromo 2,4-Dihydroxydiphenyl Methane
　4'-Bromo 2,4-Dihydroxydiphenyl Methane
Bisphenolic Compounds
　2,2'-Methylene bis (4-chlorophenol)
　2,2'-Methylene bis (3,4,6-trichlorophenol)
　2,2'-Methylene bis (4-chloro-6-bromophenol)
　bis (2-hydroxy-3,5-dichlorophenyl) sulphide
　bis (2-hydroxy-5-chlorobenzyl)sulphide
Benzoic Esters (Parabens)
　Methylparaben
　Propylparaben
　Butylparaben
　Ethylparaben
　Isopropylparaben
　Isobutylparaben
　Benzylparaben
　Sodium Methylparaben
　Sodium Propylparaben
Halogenated Carbanilides
　3,4,4'-Trichlorocarbanilides (TRICLOCARBAN® or TCC)
　3-Trifluoromethyl-4,4'-dichlorocarbanilide (CLOFLUCARBAN)
　3,3',4-Trichlorocarbanilide
Quaternary Ammonium Compounds
　Benzalkonium Chloride
　Benzethonium chloride
Biguanides
　Polyhexamethylene Biguanide Hydrochloride
　Chlorhexidine
Chlorhexidine derivatives
　Chlorhexidine Digluconate
　Chlorhexidine Dihydrochloride
　Chlorhexidine Diacetate
Chloroxylenol
Oxyquinolines
　8-Hydroxyquinoline
Iodine
Iodophers
　Povidone Iodine
Hexamidine
Alcohols
　Ethanol
　Butyl Alcohol
　Isopropanol
　2-Phenoxyethanol
Antibiotics
　Bacitracin
　Neomycin
　Polymyxin B
　Nystatin
Organic Acid and Acid Donors
　Citric Acid
　Ascorbic Acid
　Malic Acid
　Tartaric Acid
　Benzoic Acid
　Triacetin
Sphingosines
　D-sphingosine
Amphoteric Surfactants
　Dodecyl-di (amino ethyl) glycine
Ionene Polymers
　Onamer M
Modified phospholipids
　Coco amidopropyl phosphatidyl PG-dimonium chloride
　Linole amidopropyl phosphatidyl PG-dimonium chloride
　Coco phosphatidyl PG-dimonium chloride Another class of antibacterials, which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae,* Ratanhiae and *Curcuma longa.* Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, famesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional active agents are antibacterial metal salts. This class generally includes salts of metals in groups 3b-7b, 8 and 3a-5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antibacterials for use herein are the broad spectrum actives selected from the group consisting of TRICLOSAN®, TRICLOCARBAN®, OCTOPIROX®, PCMX, ZPT, natural essential oils and their key ingredients, and mixtures thereof. The most preferred antibacterial active for use in the present invention is TRICLOSAN®.

The antibacterial component comprises from about 0.1% to 6% of the lotion composition, preferably from about 0.3% to 3% and more preferably from about 0.5% to 1.5%. Though the antibacterials may be mixed with one another and/or mixed with the antivirals of this invention, some mixtures within the scope of this invention may result in the formation of a precipitate.

Some of the components of the lotion of this invention have multiple functionality. For example, citric acid and ascorbic acid have both antiviral and antibacterial functionality. Additionally, the antibacterials and some of the antivirals also act as preservatives by preventing the growth of deleterious microorganisms in the lotion composition itself.

2. Hydrophilic Solvent(s)

Another important component(s) of these lotions is the incorporation of hydrophilic solvents to aid in the solubilization of the antiviral organic acids. Suitable solvents include but are not limited to solvents having from about 1 to 150 carbon atoms wherein the carbon may be branched or straight chain, saturated or unsaturated, with or without ether linkages and containing from about 1 to 302 hydroxyl group(s). These solvents include but are not limited to glycol type solvents such as polyethylene glycols, glycerin, ethylene glycol, propylene glycol, polypropylene glycol, ethanol, isopropanol, hexylene glycol, and mixtures thereof. Preferred is polyethylene glycol having a molecular weight range of from about 200 to 3000. More preferred solvents include those solvents having from about 1 to 25 carbon atoms and from about 1 to 8 hydroxyl group(s). Even more preferred is propylene glycol and polyethylene glycols wherein the polyethylene glycols have a molecular weight range from about 200 to 1500 or mixtures thereof.

In addition to allowing solubilization of the antiviral organic acids, some of the glycol type solvents are also known to be antiviral in nature such as propylene glycol and triethylene glycol. Also, some of these glycol type solvents can provide an increase in the viscosity of the lotion and thus prevent unwanted migration of the lotion components within the fibrous paper network. These glycol based solvents can also function as humectants and thus provide a moisturization benefit to the skin. But, their primary use in this particular application is to aid in the solubilization of the antiviral organic acid. The hydrophilic solvent comprises from about 5% to 60% of the lotion composition.

3. Skin Conditioning Agent(s)

The other active ingredient(s) in these lotion compositions are one or more skin conditioning agents. As used herein, a skin conditioning agent is a material that softens, soothes, supples, coats, lubricates, moisturizes, or cleanses the skin. A skin conditioning agent typically accomplishes several of these objectives such as soothing, moisturizing, and lubricating the skin. For the purposes of the present invention, these skin conditioning agents have either a plastic or fluid consistency at 20° C., i.e., at ambient temperatures. This particular skin conditioning agent consistency allows the lotion composition to impart a soft, lubricious, lotion-like feel.

The skin conditioning agents useful in the present invention are also substantially free of water. By "substantially free of water" it is meant that water is not intentionally added to the skin conditioning agent. Addition of water to the skin conditioning agent or the lotion is not necessary in preparing or using the lotion compositions of the present invention and could require an additional drying step. In fact, it is undesirable and unnecessary to add water to these antiviral lotions. The addition of water could lead to potential microbial growth in the lotions. In addition, water would lower the melting point of the lotion and aid in the migration of other lotion components within the paper fiber substrate. This would likely have a negative impact on the tensile and caliper properties of the lotioned paper. However, minor or trace quantities of water in the skin conditioning agent that are picked up as a result of, for example, ambient humidity can be tolerated without adverse effect. Typically, the skin conditioning agents used in the present invention contain about 5% or less water, preferably about 1.0% or less water, more preferably about 0.5% or less water, and most preferably about 0.1% or less water.

Skin conditioning agents useful in the present invention can be petroleum-based such as mineral oil and petrolatum, fatty acid ester type, fatty alcohol type, dimethicones including functionalized derivatives of dimethicones, polyethylene glycols, or mixtures of these skin conditioning agents. Suitable petroleum-based skin conditioning agents include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons which are liquids at room temperature. Petrolatum usually refers to more viscous mixtures of hydrocarbons having from 16 to 32 carbon atoms. Petrolatum is a particularly preferred skin conditioning agent for lotion compositions of the present invention because of its exceptional skin moisturizing benefits.

Dimethicones and functionalized derivatives of dimethicones are also very effective paper softeners. The aminofunctional polydimethylsiloxanes are especially effective softeners for paper. Dimethicones possessing a viscosity range of about 20 to 12,500 centistokes at 25° C. are preferred. Thus, not only could a material such as dimethicone or the other skin conditioning agents mentioned above provide a soft feel to the paper and skin, but they could provide a skin protectant benefit if transferred to the skin. This benefit would be particularly advantageous if it was desirable to prevent a particularly harsh ingredient from contacting the skin.

Fatty alcohols are also particularly preferred due to their crystalline linear structure. The high melt points of the fatty alcohols raises the melt point of the lotion and thus aids in preventing migration of the lotion throughout the fiber network. The linear structure of the fatty alcohols gives the lotion crystalline attributes and should lead to faster crystallization/solidification onto the paper substrate surface. Thus, during application to the paper surface, the lotion should set up and solidify faster on the surface of the paper substrate. This concentrates the lotion at the surface and gives the lotioned paper product a superior feel and also leads to a more efficient use of the antimicrobial(s). The hydroxyl group in the fatty alcohol may also contribute to the lotion's antimicrobial action.

Suitable fatty acid ester type skin conditioning agents include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester skin conditioning agents can also be derived from esters of longer chain fatty alcohols ($C_{12}$–$C_{28}$, preferably $C_{12}$–$C_{18}$) and shorter chain fatty acids e.g., lactic acid, such as lauryl lactate and cetyl lactate.

In addition to the petroleum-based skin conditioning agents, dimethicone based skin conditioning agents, fatty acid ester skin conditioning agents, and fatty alcohol skin conditioning agents, the skin conditioning agents useful in the present invention can include minor amounts (e.g., up to about 10% of the total skin conditioning agent) of other, conventional skin conditioning agents. These other, conventional skin conditioning agents include propylene glycol, glycerin, hexylene glycol, polyethylene glycols, triethylene glycol, liposomes, spermaceti, squalene, cholesteryl, or other waxes (such as the $C_{12}$ to $C_{50}$ waxes), fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$–$C_{28}$ fatty acids; other fatty esters of polyhydroxy alcohols; lanolin and its derivatives; silicone polyether copolymers, and polysiloxanes such as aminofunctional polydimethylsiloxanes having a viscosity at 20° C. of from about 5 to about 2,000 centistokes such as disclosed in U.S. Pat. No. 5,059,282, issued to Ampulski et al. on Oct. 22, 1991, which is incorporated by reference.

The amount of skin conditioning agent that can be included in the lotion composition will depend on a variety of factors, including the particular skin conditioning agent involved, the lotion-like benefits desired, the other components in the lotion composition and like factors. The lotion composition can comprise from about 0.1% to about 60% of the skin conditioning agent, more preferably from about 5% to about 50%.

4. Hydrophilic Surfactant(s)

In many instances, lotion compositions according to the present invention will be applied to tissue paper webs that will be used as toilet tissue. In such cases, it is highly desirable that the paper web treated with the lotion composition be sufficiently wettable. Depending upon the particular immobilizing agent used in the lotion composition of the present invention, an additional surfactant, preferably a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of a hydrophilic surfactant. Other immobilizing agents such as the $C_{16}$–$C_{18}$ fatty alcohols and waxes having HLB values below about 7 will require addition of a hydrophilic surfactant to improve wettability if the lotion composition is applied to paper webs used as toilet tissue. Similarly, a hydrophobic skin conditioning agent such as petrolatum or mineral oil will require the addition of a hydrophilic surfactant. It should be noted that water absorbency will be more critical in a product such as toilet tissue. A lotion applied to a facial tissue may not require a surfactant for purposes of absorbency. However, a surfactant may be required in order to emulsify and stabilize the hydrophilic and hydrophobic components contained in the lotion.

Suitable hydrophilic surfactants will be miscible with the skin conditioning agent, the optional immobilizing agent and other ingredients in the composition so as to form homogeneous mixtures. Because of possible skin sensitivity of those using paper products to which the lotion composition is applied, these surfactants should also be relatively mild and non-irritating to the skin. Typically, these hydrophilic surfactants are nonionic as this type of surfactant tends to be less irritating to the skin then anionic and cationic surfactants. Additionally, the nonionic surfactants are also easier to formulate into the lotion compositions of the present invention. The higher melting nonionic surfactants are prefered.

Since maintaining skin mildness is an important factor in the production of lotioned tissue products, the use of non-ionic surfactants is preferred since they are milder to the skin than charged surfactants. This is not to state that all charged surfactants are irritating to the skin. But, as a general rule, most charged surfactants are irritating to the skin. The non-ionic surfactants used in these antimicrobial lotions serve several important functions. One critical function is to allow the hydrophilic acid/solvent mixture to mix with the hydrophobic skin conditioning agents. This allows for a stable blend of the hydrophobic components to be made with the hydrophilic components.

In addition to providing lotion stability, the surfactant also allows the lotioned paper to absorb water and mucus at a reasonable rate. If no surfactant was formulated into the lotion, the lotioned paper product in some cases might repel water and mucus thereby possibly causing negative consumer reactions. Lotion formulations consisting of no surfactant and such hydrophobic skin conditioning agents as petrolatum, mineral oil, and dimethicone would be especially hydrophobic. As noted, the inclusion of the surfactant also aids in solubilizing organic acids into these hydrophobic skin conditioning agents.

It is important for the lotioned tissue paper (especially in the case of toilet tissue) according to the present invention to be absorbent and/or wettable, as reflected by its hydrophilicity. Hydrophilicity of tissue paper refers, in general, to the propensity of the tissue paper to be wetted with water. Hydrophilicity of tissue paper can be quantified somewhat by determining the period of time required for dry tissue paper to become completely wetted with water. This period of time is referred to as the "wetting" (or "sinking") time. In order to provide a consistent and repeatable test for wetting time, the following procedure can be used for wetting time determinations: first, a paper sample (the environmental conditions for testing of paper samples are 23±1° C. and 50±2% RH. as specified in TAPPI Method T 402), approximately 2.5 inch×3.0 inches (about 6.4 cm×7.6 cm) is cut from an 8 sheet thick stack of conditioned paper sheets; second, the cut 8 sheet thick paper sample is placed on the surface of 2500 ml. of distilled water at 23±1° C. and a timer is simultaneously started as the bottom sheet of the sample touches the water; third, the timer is stopped and read when wetting of the paper sample is completed, i.e. when the top sheet of the sample becomes completely wetted. Complete wetting is observed visually.

The preferred hydrophilicity of tissue paper depends upon its intended end use. It is desirable for tissue paper used in a variety of applications, e.g., toilet paper, to completely wet in a relatively short period of time to prevent clogging once the toilet is flushed. Typically, wetting time is 4 minutes or less, preferably, wetting time is 90 seconds or less, more preferably 30 seconds or less, and most preferably, wetting time is 10 seconds or less.

The hydrophilicity of tissue paper can, of course, be determined immediately after manufacture. However, substantial increases in hydrophobicity can occur during the first two weeks after the tissue paper is made: i.e. after the paper has aged two (2) weeks following its manufacture. Thus, the above stated wetting times are preferably measured at the end of such two week period. Accordingly, wetting times measured at the end of a two week aging period at room temperature are referred to as "two week wetting times."

The higher melting non-ionic surfactants can also contribute to hardening of the lotion and thus aid in confining the lotion at the surface of the paper substrate. Importantly in relation to antiviral activity, the surfactant can function to aid in solubilizing the lipid shell layer of the enveloped class of viruses. This solubilization of the lipid shell enhances the ability of the antiviral acids to penetrate into the virus structure and deactivate it. It should be noted that the lotion of this invention may potentially be made without adding a hydrophilic surfactant, depending upon which hydrophilic solvent is used, the melting point of the lotion, the desired end use of the paper (i.e.; toilet tissue or facial tissue), or if the lotion is applied to the paper in a discontinuous pattern such that some areas of the paper are covered with lotion while others are not.

Suitable nonionic surfactants will be substantially non-migratory after the lotion composition is applied to the tissue paper web and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of tissue paper products, e.g., at least about 30° C. In this regard, these nonionic surfactants will preferably have melting points similar to those of the optional immobilizing agents.

Suitable nonionic surfactants for use in lotion compositions of the present invention include alkylglycosides; alkylglycoside ethers as described in U.S. Pat. No. 4,011,389, issued to Langdon et al. on Mar. 8, 1977; alkylpolyethoxylated esters such as PEGOSPERSE 1000MS, available from Lonza Inc. of Fair Lawn, N.J.; ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20), TWEEN 20 (sorbitan esters of lauric acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 8 to about 22 carbon atoms with an average of about 2 to 30 moles of ethylene oxide per mole of alcohol.

Examples of such ethoxylated alcohols include the condensation products of myristyl alcohol with an average of about 7 moles of ethylene oxide per mole of alcohol, the condensation products of cetearyl alcohol with about 2 to 20 average moles of ethylene oxide, the condensation products of stearyl alcohol with about 2 to 20 average moles of ethylene oxide, the condenstion products of cetyl alcohol with 2 to 20 average moles of ethylene oxide, the condensation products of lauryl alcohol with 2 to 20 average moles of ethylene oxide, and the condensation products of coconut alcohol (a mixture of fatty alcohols having alkyl chains varying in length from 10 to 14 carbon atoms) with an average of about 6 moles of ethylene oxide. A number of suitable ethoxylated alcohols are commercially available, including TERGITOL 15-S-9 (the condensation product of $C_{11}$–$C_{15}$ linear alcohols with an average of about 9 moles of ethylene oxide), marketed by Union Carbide Corporation of Danbury, Conn.; the NEODOL brand name surfactants marketed by Shell Oil Co. of Houston, Tex., in particular NEODOL 25-12 (condensation product of $C_{12}$–$C_{15}$ linear alcohols with an average of about 12 moles of ethylene oxide) and NEODOL 23-6.5T (condensation product of $C_{12}$–$C_{13}$ linear alcohols with an average of about 6.5 moles of ethylene oxide that has been distilled (topped) to remove certain impurities), and especially the PLURAFAC brand name surfactants marketed by BASF Corp. of Mount Olive, N.J., in particular PLURAFAC A-38 (a condensation product of a $C_{18}$ straight chain alcohol with an average of about 27 moles of ethylene oxide). (Certain of the hydrophilic surfactants, in particular ethoxylated alcohols such as NEODOL 25-12, can also function as alkyl ethoxylate skin conditioning agents). Other examples of preferred ethoxylated alcohol surfactants are supplied by Imperial Chemical Company (ICI) of Wilmington, Del. These include the class of BRIJ surfactants and mixtures thereof, with BRIJ 76 (i.e., Steareth-10) and BRIJ 56 (i.e., Ceteth-10) being especially preferred. As noted, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes AEROSOL OT, a dioctyl ester of sodium sulfosuccinic acid marketed by Cytec Industries Inc. of West Paterson, N.J.

Still other types of suitable surfactants for use in the present invention, made by General Electric of Fairfield, Conn., include silicone copolymers such as General Electric's SF 1188 (a copolymer of a polydimethylsiloxane and a polyoxyalkylene ether) and General Electric's SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition. These silicone surfactants as well as other dimethicone copolyols can also be effective in emulsifying non-functionalized dimethicone fluids such as General Electric's SF96-20, SF96-50, SF96-100, and SF96-350.

The amount of hydrophilic surfactant required to increase the wettability of the lotion composition to a desired level will depend upon the HLB value of the surfactant, the concentration of immobilizing agent used, the HLB value of the other ingredients in the formulation and like factors. The lotion composition can comprise from about 0.1% to about 60% of the hydrophilic surfactant when needed to increase the wettability properties of the composition. Preferably, the lotion composition comprises from about 5% to about 50%, and most preferably from about 10% to 30% of the hydrophilic surfactant.

5. Optional Immobilizing Agent(s)

An optional component of the lotion compositions of the present invention is an agent(s) capable of immobilizing the skin conditioning agent n the surface of the paper to which the lotion composition is applied. Because some of the skin conditioning agents, surfactants, solvents and optional ingredients in the composition have a plastic or fluid consistency at 20° C., they tend to flow or migrate, even when subjected to modest shear. When applied to a tissue paper web, especially in a melted or molten state, the skin conditioning agent will not remain primarily on the surface of the paper. Instead, the skin conditioning agent will tend to migrate and flow into the interior of the paper.

This migration of the skin conditioning agent into the interior of the paper can cause undesired debonding of the paper by interfering with the normal hydrogen bonding that takes place between the paper fibers. This usually leads to a decrease in tensile strength of the paper. It also means much more skin conditioning agent has to be applied to the paper to get the desired lubricious, lotion-like feel benefits at the surface of the paper. Increasing the level of skin conditioning agent not only increases the cost, but also exacerbates the debonding problem of the paper. The caliper can also be negatively impacted if no immobilizing agent is used. With no immobilizer, the lotion migrates throughout the fibers of the paper instead of concentrating itself at the surface of the paper. In severe cases where liquid skin conditioning agents are employed, the caliper can actually decrease.

The immobilizing agent counteracts this tendency of the skin conditioning agent to migrate or flow by keeping the skin conditioning agent primarily localized on the surface of the paper to which the lotion composition is applied. This is believed to be due, in part, to the fact that the immobilizing agent forms hydrogen bonds with the paper. Through this hydrogen bonding, the immobilizing agent becomes localized on the surface of the paper. Since the immobilizing agent is also miscible with the skin conditioning agent (or solubilized in the skin conditioning agent with the aid of an appropriate emulsifier), it entraps the skin conditioning agent on the surface of the paper as well. Immobilization is also enhanced by a more crystalline structure of the immobilizing agent. If the immobilizing agent is more crystalline in structure, the immobilization molecules will tend to quickly form seeds of nucleation sites where the lotion can solidify. The more amorphous immobilization agents tend to solidify at slower rates than their more crystalline counterparts.

However, some amorphous high melting microcrystalline waxes can be effective in trapping the lower molecular weight hydrocarbon components of mineral oil and petrolatum. This trapping effect can aid in preventing the skin conditioning agent system from migrating throughout the paper structure. Thus, even though their crystallization kinetics may be slower than their paraffinic wax counterparts, the amorphous high melting microcrystalline waxes can be effective in inhibiting flow of the liquid hydrocarbon components. In addition, the highly branched immobilization agents, such as the microcrystalline waxes, can increase the viscosity of the lotion. This viscosity increase can also aid in maintaining the lotion at the surface of paper by increasing the resistance to flow into the bulk of the paper. Thus, it is advantageous to have a lotion which both crystallizes and solidifies quickly at the surface of the paper while at the same time having a high viscosity to reduce the flow of the lotion into the bulk of the paper.

It is also advantageous to lock the immobilizing agent on the surface of the paper. As previously noted, this can be accomplished by using immobilizing agents which quickly crystallize (i.e., solidify) at the surface of the paper. In addition, outside cooling of the treated paper via blowers, fans, etc. can speed up crystallization of the immobilizing agent.

In addition to being miscible with (or solubilized in) the skin conditioning agent, the immobilizing agent needs to have a melting point of at least about 25° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

The viscosity of the immobilizing agent should also be as high as possible to keep the lotion from flowing into the interior of the paper. Unfortunately, high viscosities can also lead to lotion compositions that are difficult to apply without processing problems. Therefore, a balance must be achieved so that the viscosities are high enough to keep the immobilizing agent localized on the surface of the paper, but not so high as to cause processing problems. Suitable viscosities for the immobilizing agent will typically range from about 5 to about 200 centipoises, preferably from about 15 to about 100 centipoises, measured at 60° C.

Suitable immobilizing agents for the present invention can comprise $C_{12}$–$C_{22}$ fatty alcohols; $C_{12}$–$C_{22}$ fatty acids; sorbitan stearates; sorbitan alkylates; polyoxylated sorbitan mono-, di-, and tri-alkylates; sorbitan mono-, di-, and tri-alkylates; clays; waxes; and mixtures thereof. Preferred immobilizing agents include $C_{16}$–$C_{18}$ fatty alcohols, most preferably cetyl alcohol, stearyl alcohol, and mixtures thereof. Mixtures of cetyl alcohol and stearyl alcohol are particularly preferred. Behenyl alcohol ($C_{22}$) is also an excellent and commercially available fatty alcohol to use as an immobilizing agent in the current formulas. Other preferred immobilizing agents include $C_{16}$–$C_{18}$ fatty acids, most preferably palmitic acid, stearic acid, and mixtures thereof. Mixtures of palmitic acid and stearic acid are particularly preferred. Still other preferred immobilizing agents include paraffin type waxes, sorbitan stearates, and mixtures thereof. Preferably, the fatty alcohols and fatty acids are linear.

Importantly, these preferred immobilizing agents such as the $C_{16}$–$C_{18}$ and $C_{22}$ fatty alcohols increase the rate of crystallization of the lotion causing the lotion to crystallize rapidly onto the surface of the substrate. Lower lotion levels can therefore be utilized so a superior lotion feel can be delivered. Traditionally, greater amounts of lotion were needed to generate softness because of the flow of these liquids into the bulk paper substrate.

Other types of immobilizing agents can be used in combination or in place of the fatty alcohols, fatty acids, sorbitan stearates and waxes described above. Typically, only minor amounts of these other types of immobilizing agents would be used (i.e., up to about 10% of the total immobilizing agent). However, using larger amounts of these other types of these immobilizing agents (i.e., up to 100%) is within the scope of the present invention. Examples of these other types of immobilizing agents includes polyhydroxy fatty acid esters, polyhydroxy fatty acid amides, clays, clay derivatives, and mixtures thereof. To be useful as immobilizing agents, the polyhydroxy moiety of the ester or amide should have at least one free hydroxy group. It is believed that these free hydroxy group(s) are the ones that co-crosslink by forming hydrogen bonds with the cellulosic fibers of the tissue paper web to which the lotion composition is applied as well as homo-crosslink, by forming hydrogen bonds with the hydroxy groups of the alcohol, acid, ester or amide, thus entrapping and immobilizing the other components in the lotion matrix.

It is also believed that molecules such as long chain fatty alcohols can orient themselves and interact with one another to form a lamellar structure. In this lamellar structure, the hydroxyl groups and alkyl chains of neighboring alcohol molecules orient and interact with one another to form an organized structure. In this packing arrangement, the hydroxyl groups of the alcohols form hydrogen bonds with the cellulose polar functionalities (e.g., hydroxy or carbonyl) to immobilize the alcohols at the paper's surface. Since the alcohols are miscible with the preferred skin conditioning agents, anchoring and/or immobilization of the skin conditioning agent will occur.

Preferred esters and amides will have three or more free hydroxy groups on the polyhydroxy moiety and are typically nonionic in character. Because of the possible skin sensitivity of those using paper products to which the lotion composition is applied, these esters and amides should also be relatively mild and non-irritating to the skin.

Suitable polyhydroxy fatty acid esters for use in the present invention will have the formula:

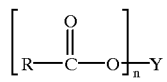

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40 manufactured by ICI Chemicals), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. of Fair Lawn, N.J. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters are particularly preferred and include sucrose monostearate and sucrose monolaurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927, issued to Honsa on Dec. 29, 1992 and incorporated herein by reference, which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl,. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

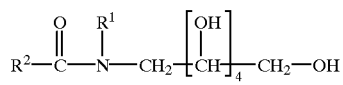

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the skin conditioning agent. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the skin conditioning agent such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of steareth-2 and sorbitan tristearate as the emulsifier.

The amount of immobilizing agent that should be included in the lotion composition will depend on a variety of factors, including the particular skin conditioning agent involved, the particular immobilizing agent involved, whether an emulsifier is required to solubilize the immobilizing agent in the skin conditioning agent, the other components in the lotion composition and like factors. The lotion composition comprises from about 5% to 60% of the immobilizing agent and preferably from about 10% to 40% of the immobilizing agent.

6. Other Optional Components

Lotion compositions can comprise other optional components typically present in emollients, creams, and lotions of this type. These optional components include viscosity modifiers, perfumes, disinfectants, pharmaceutical actives, film formers, vitamins (e.g. vitamin E), deodorants, opacifiers, astringents, solvents and the like. In addition, stabilizers can be added to enhance the shelf life of the lotion composition such as cellulose derivatives, proteins, antioxidants and lecithin. All of these materials are well known in the art as additives for such formulations and can be employed in appropriate amounts in the lotion compositions of the present invention. In addition, natural essential oils such as camphor, thymol, pine oil, menthol, eucalyptol (cineole), geraniol, lemon oil, methyl salicylate, clove and other similar materials may be used to give the product a medicinal scent. In addition, some of these natural essential oils also possess antiviral and antibacterial properties. These other optional components may comprise from about 0.1% to 20% of the lotion composition.

C. Treating Tissue Paper With Lotion Composition

In preparing lotioned paper products according to the present invention, the lotion composition may be applied to at least one surface of a tissue paper web. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the surface of the paper web. The lotion composition can be applied either to one surface of the tissue paper web, or both surfaces. Preferably, the lotion composition is applied to both surfaces of the paper web.

The manner of applying the lotion composition to the tissue paper web should be such that the web does not become saturated with the lotion composition. If the web becomes saturated with the lotion composition, there is a greater potential for debonding of the paper to occur, thus leading to a decrease in the tensile strength of the paper. Also, saturation of the paper web is not required to obtain the softness and lotion-like feel benefits from the lotion composition of the present invention. Particularly suitable application methods will apply the lotion composition primarily to the ,surface, or surfaces of the paper web. The saturation of the center ply of a three ply tissue would be an example of where the tissue paper might be saturated with a more liquid-like lotion compostion. Even though the physical properties of the middle ply would likely be adversely affected, it would still function as an effective carrier of the lotion. Of course, materials that could migrate from this center ply to the outside plies and adversely affect their physical properties would have to be avoided.

The lotion composition can be applied to the tissue paper web after the web has been dried, i.e. a "dry web" addition method. The lotion composition is applied in an amount of from about 2 to about 40% by weight of the tissue paper web. Preferably, the lotion composition is applied in an amount of from about 5 to about 25% by weight of the tissue paper web, most preferably from about 10 to about 18% by weight of the web. Such relatively low levels of lotion composition are adequate to impart the desired softness and lotion-like feel benefits to the tissue paper, yet do not saturate the tissue paper web to such an extent that absorbency, wettability and particularly, strength, are substantially affected. The amount of lotion on the paper must also be optimized in order to achieve effective virus and bacteria kill within the paper structure.

The lotion composition can also be applied non-uniformly to the surface(s) of the tissue paper web. By "non-uniform" is meant that the amount, pattern of distribution, etc. of the lotion composition can vary over the surface of the paper. For example, some portions of the surface of the tissue paper web can have greater or lesser amounts of lotion composition, including portions of the surface that do not have any lotion composition on it. An example of non-uniform application is where the tissue structure contains differing amounts and differing compositions of various formulations throughout its structure or alternatively where some zones may contain no lotion at all as taught by U.S. Pat. No. 4,481,243 issued to Allan on Nov. 6, 1984 and incorporated herein by reference. For instance in a two ply tissue structure, an attractive feeling skin conditioning agent composition containing antibacterial agents might be applied to the two outer surfaces of the paper structure while an antiviral composition is applied to the two inner surfaces of the paper structure. Or in a three ply paper structure, the inside ply might contain the antiviral lotion composition while the consumer side of the two outside plies contains a skin conditioning agent composition and an antibacterial agent.

Additional examples include adding a skin conditioning agent not containing any antimicrobial active to the outside plies. The skin conditioning agent might be an ingredient such as dimethicone which would transfer to the skin upon wiping to form a protective layer on the skin. In addition, this skin conditioning agent composition could lead to a more superior feeling lotion than the antimicrobial composition. Or, this skin conditioning agent layer might transfer another active to the skin such as a sunblock, or skin healing additive. While this skin conditioning agent composition would be applied to the outside plies, the antimicrobial active composition could be applied on the inside of one or both outside plies to produce the antimicrobial killing activity within the tissue. With the antimicrobial active on the inside of the tissue, and the skin conditioning agent applied to the outside, the antimicrobial killing activity would most probably be confined to the inside of the tissue rather than the user's skin surface. The antimicrobial composition could also be applied to a third ply which is sandwiched between the two outer plies containing the skin conditioning agent. Both of these schemes present certain advantages in that a unique active can be transferred to the skin. In addition, if a very high concentration of organic acid is used on the inside of the tissue, the skin conditioning agent transfer to the skin could form a protective barrier from any adverse skin reactions as potentially caused by the use of an irritating acid. There are numerous permutations of these approaches.

The lotion composition can be applied to the tissue paper web at any point after it has been dried. For example, the lotion composition can be applied to the tissue paper web after it has been creped from a Yankee dryer, but prior to calendering, i.e., before being passed through calender rolls. The lotion composition can also be applied to the paper web after it has passed through such calender rolls and prior to being wound up on a parent roll. Usually, it is preferred to apply the lotion composition to the tissue paper as it is being unwound from a parent roll and prior to being wound up on smaller, finished paper product rolls.

The lotion composition is typically applied from a melt thereof to the tissue paper web. Since the lotion composition melts at significantly above ambient temperatures, it is usually applied as a heated coating to the tissue paper web. Typically, the lotion composition is heated to a temperature in the range from about 35° to about 100° C., preferably from 40° to about 90° C., prior to being applied to the tissue paper web. Once the melted lotion composition has been applied to the tissue paper web, it is allowed to cool and solidify to form solidified coating or film on the surface of the paper. To allow more lotion to solidify at the surface of the tissue rather than into the bulk of the paper, fans or chill rolls can be directed at the lotioned paper to hasten the lotion solidification.

The lotion compositions of the present invention may be applied to the tissue paper by spraying the composition onto the tissue paper web or by gravure coating and extrusion coating methods. Gravure coating and extrusion coating methods are preferred such as those taught by U.S. Pat. No. 5,246,546, issued to Ampulski on Sep. 21, 1996 and incorporated herein by reference. FIG. 1, illustrates one such preferred application method involving gravure coating. Referring to FIG. 1, a dried tissue web 1 is unwound from parent tissue roll 2 (rotating in the direction indicated by arrow 2a) and advanced around turning roll 4. From turning roll 4, web 1 is advanced to offset-gravure coating station 6 where the lotion composition is then applied to both sides of the web. After leaving station 6, web 1 becomes a lotioned web indicated by 3. Lotioned web 3 is then advanced around turning roll 8 and then wound up on lotioned tissue parent roll 10 (rotating in the direction indicated by arrow 10a).

Station 6 comprises a pair of linked offset-gravure presses 12 and 14. Press 12 consists of a lower gravure cylinder 16 and an upper offset cylinder 18; press 14 similarly consists of a lower gravure cylinder 20 and an upper offset cylinder 22. Gravure cylinders 16 and 20 each have a specific etched cell pattern and size, and each have a chrome plated surface, while offset cylinders 18 and 22 each have a smooth polyurethane rubber surface. The size of the cell volume of the gravure roll will depend upon the desired coat weight, line speed, and lotion viscosity. Both the gravure and offset cylinders are heated to keep the lotion molten. These gravure and offset cylinders rotate in the directions indicated by arrows 16a, 18a, 20a and 22a, respectively. As shown in FIG. 1, offset cylinders 18 and 22 are directly opposite and parallel to each other and provide a nip area indicated by 23 through which web 1 passes.

Positioned beneath gravure cylinders 16 and 20 are fountain trays 24 and 26, respectively. Hot, molten (e.g., 65° C.) lotion composition is pumped into each of these heated trays 24 and 26 to provide reservoirs of the molten lotion composition, as indicated by arrows 30 and 32, respectively. As gravure cylinders 16 and 20 rotate in the directions indicated by arrows 16a and 20a within reservoirs 30 and 32, they pick up a quantity of molten lotion composition. Excess lotion on each of the gravure cylinders 16 and 20 is then removed by doctor blades 34 and 36, respectively.

The lotion composition remaining in the heated gravure cylinder cells 16 and 20 is then transferred to heated offset cylinders 18 and 22 (rotating in the opposite direction as indicated by arrows 18a and 22b) in nip areas 38 and 40 between the respective pairs of cylinders. The lotion composition transferred to offset cylinders 18 and 22 is then simultaneously transferred to both sides of web 1. The amount of lotion composition transferred to web 1 can be controlled by: (1) adjusting the width of nip area 23 between offset cylinders 18 and 22; and/or (2) adjusting the width of nip areas 38 and 40 between gravure/offset cylinder pairs 16/18 and 20/22.

Figure 2:
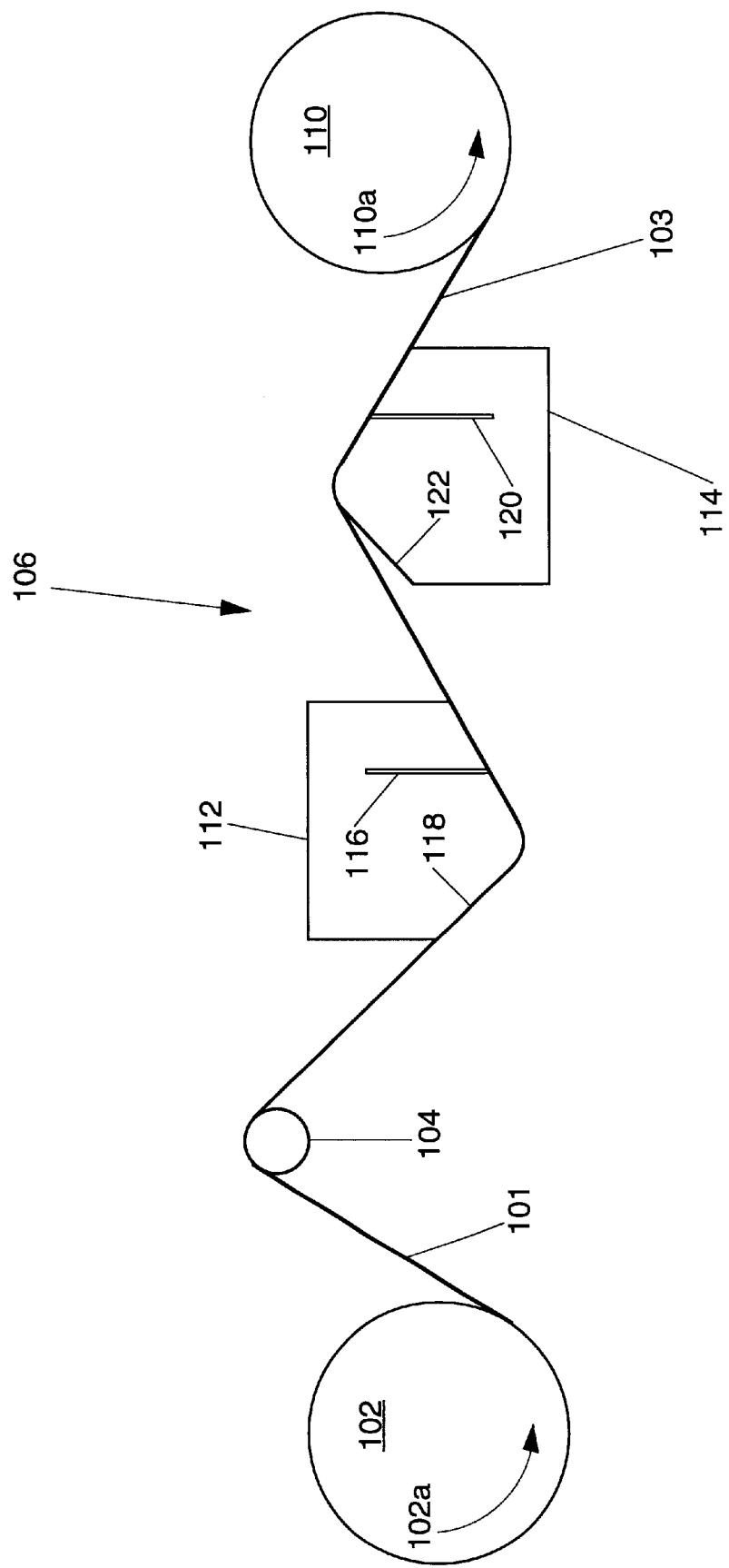
FIG. 2 is a schematic representation illustrating an alternative process for applying the lotion composition of the present invention to tissue paper webs.

FIG. 2 illustrates an alternative preferred method involving slot extrusion coating. Referring to FIG. 2, a dried tissue web 101 is unwound from parent tissue roll 102 (rotating in the direction indicated by arrow 102a) and then advanced around turning roll 104. From turning roll 104, web 101 is advanced to slot extrusion coating station 106 where the lotion composition is then applied to both sides of the web. After leaving station 106, web 101 becomes a lotioned web indicated by 103. Lotioned web 103 is then wound up on lotioned tissue parent roll 110 (rotating in the direction indicated by arrow 110a).

Station 106 comprises a pair of spaced slot extruders 112 and 114. Extruder 112 has an elongated slot 116 and a web contacting surface 118; extruder 114 similarly has an elongated slot 120 and a web contacting surface 122. As shown in FIG. 2, extruders 112 and 114 are oriented such that surface 118 is in contact with one side of web 101, while surface 122 is in contact with the other side of web 101. Hot, molten (e.g., 65° C.) lotion composition is pumped to each of extruders 112 and 114 and is then extruded through slots 116 and 120, respectively.

As web 101 passes over the heated surface 118 of extruder 112 and reaches slot 116, the molten lotion composition extruded from slot 116 is applied to the side of web 101 in contact with surface 118. Similarly, as web 101 passes over heated surface 122 of extruder 114 and reaches slot 120, the molten lotion composition extruded from slot 120 is applied to the side of web 101 in contact with surface 122. The amount of lotion composition transferred to web 101 is controlled by: (1) the rate at which the molten lotion composition is extruded from slots 116 and 122; and/or (2) the speed at which web 101 travels while in contact with surfaces 118 and 122.

Specific Illustrations of the Preparation of Lotioned Tissue Paper According to the Present Invention The following are specific illustrations of treating tissue paper with lotion compositions in accordance with the present invention:

EXAMPLE 1

A. Preparation of Lotion Composition A

The water free Lotion Composition A is made by first mixing the following components together: propylene glycol, polyoxyethylene(4) lauryl ether (Brij 30 or equivalent), and polyoxyethylene(10) cetyl ether (Brij 56 or equivalent). This mixture is heated to 60 to 90° C. and mixed until a clear, transparent, and colorless solution results. While mixing and maintaining this solution temperature in the range of 60 to 90° C., the salicylic acid is added. This mixture is mixed and heated in the range of 60 to 90° C. until a clear, transparent, and colorless solution results. While mixing and maintaining this solution temperature in the range of 60 to 90° C., the cetearyl alcohol is added. This mixture is mixed and heated in the range of 60 to 90° C. until a clear, transparent, and colorless solution results. While mixing and maintaining this solution temperature in the range of 60 to 90° C., the mineral oil is added. This mixture is mixed and heated in the range of 60 to 90° C. until a clear, phase stable, transparent, and colorless solution results. The weight percentages of these components are shown in Table I below:

TABLE I

Lotion Composition A

| Component | Weight % |
| --- | --- |
| Polyoxyethylene (4) lauryl ether | 12.0% |
| polyoxyethylene (10) cetyl ether | 12.2% |
| Propylene Glycol | 26.0% |
| Salicyclic Acid | 39.6% |
| Cetearyl Alcohol | 5.2% |
| Mineral Oil | 5.0% |

EXAMPLE 2

B. Preparation of Lotion Composition B

The water free Lotion Composition B is made by first mixing the following components together: propylene glycol, polyoxyethylene(4) lauryl ether (Brij 30 or equivalent), and polyoxyethylene(10) cetyl ether (Brij 56 or equivalent). This mixture is heated to 60 to 90° C. and mixed until a clear, transparent, and colorless solution results. While mixing and maintaining this solution temperature in the range of 60 to 90° C., citric acid is added. This mixture is mixed and heated in the range of 60 to 90° C. until a clear, transparent, and colorless solution results. While mixing and maintaining this solution temperature in the range of 60 to 90° C., the cetearyl alcohol is added. This mixture is mixed and heated in the range of 60 to 90° C. until a clear, transparent, and colorless solution results. While mixing and maintaining this solution temperature in the range of 60 to 90° C., the mineral oil is added. This mixture is mixed and heated in the range of 60 to 90° C. until a dear, phase stable, transparent, and colorless solution results. The weight percentages of these components are shown in Table II below:

TABLE II

Lotion Composition B

| Component | Weight % |
| --- | --- |
| Polyoxyethylene (4) lauryl ether | 17.0% |
| Polyoxyethylene (10) cetyl ether | 5.6% |
| Propylene Glycol | 24.9% |
| Citric Acid | 41.4% |
| Cetearyl Alcohol | 5.6% |
| Mineral Oil | 5.5% |

EXAMPLE 3

C. Preparation of Lotion Composition C

The water free Lotion Composition C is made by first mixing the following components together: propylene glycol, polyoxyethylene(20) sorbitan monolaurate (Tween 20 or equivalent), and polyoxyethylene(4) sorbitan monostearate (Tween 61 or equivalent). This mixture is heated to 60 to 90° C. and mixed until a clear, transparent, and slightly yellow solution results. While mixing and maintaining this solution temperature in the range of 60 to 90° C., citric acid is added. This mixture is mixed and heated in the range of 60 to 90° C. until a clear, phase stable, transparent, and slightly yellow solution results. The weight percentages of these components are shown in Table III below:

TABLE III

Lotion Composition C

| Component | Weight % |
| --- | --- |
| Polyoxyethylene (20) sorbitan monolaurate | 10.1% |
| Polyoxyethylene (4) sorbitan monostearate | 10.3% |
| Propylene Glycol | 29.9% |
| Citric Acid | 49.7% |

EXAMPLE 4

D. Preparation of Lotion Composition D

The water free Lotion Composition D is made by first mixing the petrolatum with the cetearyl alcohol. This mixture is heated to 70 to 90° C. and mixed until a clear, transparent, and slightly yellow solution results. While mixing and maintaining this solution temperature in the range of 70 to 90° C., the ceteareth-10 is added. This mixture is mixed and heated in the range of 70 to 90° C. until a clear, transparent, and slightly yellow solution results. While mixing and maintaining this solution temperature in the range of 70 to 90° C., the salicylic acid is added. This mixture is mixed and heated in the range of 70 to 90° C. until a clear, transparent, and slightly yellow solution results. While mixing and maintaining this solution temperature in the range of 70 to 90° C., the TRICLOSAN® is added. This mixture is mixed and heated in the range of 70 to 90° C. until a clear, phase stable, transparent, and slightly yellow solution results. The weight percentages of these components are shown in Table IV below:

TABLE IV

Lotion Composition D

| Component | Weight % |
| --- | --- |
| Petrolatum | 41.0% |
| Cetearly Alcohol | 28.6% |
| Ceteareth-10 | 15.2% |
| Salicyclic Acid | 10.1% |
| TRICLOSAN ™ | 5.1% |

EXAMPLE 5

E. Preparation of Lotion Composition E

The water free Lotion Composition E is made by first mixing the following components together: propylene glycol, polyoxyethylene(4) lauryl ether (Brij 30 or equivalent), and polyoxyethylene(10) cetyl ether (Brij 56 or equivalent). This mixture is heated to 60 to 90° C. and mixed until a clear, transparent, and colorless solution results. While mixing and maintaining this solution temperature in the range of 60 to 90° C., the citric acid is added. This mixture is mixed and heated in the range of 60 to 90° C. until a clear, transparent, and colorless solution results. While mixing and maintaining this solution temperature in the range of 60 to 90° C., the cetearyl alcohol is added. This mixture is mixed and heated in the range of 60 to 90° C. until a clear, transparent, and colorless solution results. While mixing and maintaining this solution temperature in the range of 60 to 90° C., the TRICLOSAN® is added. This mixture is mixed and heated in the range of 60 to 90° C. until a clear, transparent, and colorless solution results. While mixing and maintaining this solution temperature in the range of 60 to 90° C., the mineral oil is added. This mixture is mixed and heated in the range of 60 to 90° C. until a clear, phase stable, transparent, and colorless solution results. The weight percentages of these components are shown in Table I below:

TABLE V

Lotion Composition E

| Component | Weight % |
| --- | --- |
| Polyoxyethylene (4) lauryl ether | 11.5% |
| polyoxyethylene (10) cetyl ether | 11.6% |
| Propylene Glycol | 24.6% |
| Citric Acid | 37.5% |
| Cetearyl Alcohol | 4.9% |
| Mineral Oil | 4.8% |
| TRICLOSAN ™ | 5.1% |

B. Preparation of Lotioned Tissue by Hot Melt Spraying

Lotion A, B, or C are separately placed into a PAM 600S Spraymatic hot melt spray gun (made by PAM Fastening Technology, Inc.) operating at a temperature of ~70 to 90° C. Twelve inch by 12 inch sheets of tissue paper substrate are spray coated to the desired lotion level on each side of the substrate. The lotioned tissues are then placed in a 70° C. convection oven for 30 seconds after each side are sprayed to remove volatile components, and to insure a more even coating of the lotion onto the paper fibers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A lotioned tissue comprising:
   a tissue paper having a basis weight of 40 g/m² or less, a lotion composition disposed thereon, wherein said lotion composition is semi-solid or solid at 20° C., said lotion composition comprising:
   (A) at least one antimicrobial wherein said antimicrobial is an antiviral, bacitracin, neomycin, poltymyxin B, nystatin benzalkonium chloride, benzethonium chloride, chlorhexidine, polyhexamethylene biguanide hydrochloride, methylparaben, propylparaben, TRICLOCARBAN®, OCTOPIROX®, TRICLOSAN®, povidone iodine, chloroxylenol, PCMZ, ZPT, KATHON CG®, CLOFLUCARBAN, sodium omadine, natural essential oils, 8-hydroxyquinoline, D-sphingosine, hexamidine, imidazolidinyl urea, hinokitiol, eugenol, citric acid, ascorbic acid, malic acid, tartaric acid, benzoic acid, triacetin, onamer M, ethanol, butyl alcohol, isopropanol, 2-phenoxyethanol, coco amidopropyl phosphatidyl PG-dimonium chloride, linole amidopropyl phosphatidyl PG-dimonium chloride, and coco phosphatidyl PG-dimonium chloride;
   (B) at least one hydrophilic solvent wherein said hydrophilic solvent is glycerine, ethylene glycol, polypropylene glycol, ethanol, isopropanol, hexylene glycol, propylene glycol, polyethylene glycol having a molecular weight range from about 200 to 1500, and mixtures thereof;
   (C) at least one skin conditioning agent; and
   (D) at least one hydrophilic surfactant.

2. The tissue paper of claim 1 wherein said lotion composition is applied to at least one surface of said tissue paper.

3. The tissue paper of claim 1 wherein said lotion composition is applied to said tissue paper in an amount ranging from about 2% to about 40% by weight of the dried tissue paper.

4. The tissue paper of claim 1 wherein said antimicrobial is selected from the group consisting of antivirals, antibacterials, and mixtures thereof.

5. The tissue paper of claim 1 wherein said antiviral is an organic acid.

6. The tissue paper of claim 5 wherein said organic acid comprises from about 1% to about 60% of said lotion composition.

7. The tissue paper of claim 6 wherein said organic acid is selected from the group consisting of $C_1$–$C_{12}$ saturated and unsaturated carboxylic acids possessing 1 to 4 carboxylic acid groups and having at least one hydroxyl group substituted on the $C_2$ alpha carbon; $C_1$–$C_{12}$ saturated, unsaturated, and aromatic carboxylic acids possessing 1 to 4 carboxylic acid groups and having at least one hydroxyl group substituted on the $C_3$ beta carbon, $C_1$–$C_{12}$ saturated, unsaturated, and aromatic carboxylic acids possessing 1 to 4 carboxylic acid groups; $C_1$–$C_{12}$ saturated, unsaturated, and aromatic carboxylic acids possessing 1 to 4 carboxylic acid groups and having a hydroxyl group(s) substituted on carbon number(s) $C_4$ or above; and mixtures thereof.

8. The tissue paper of claim 7 wherein said organic acid is a solid at room temperature.

9. The tissue paper of claim 6 wherein said organic acid is selected from the group consisting of citric acid, salicylic acid, tartaric acid, ascorbic acid, and mixtures thereof.

10. The tissue paper of claim 7 further comprising an inorganic acid selected from the group consisting of hydrochloric acid, boric acid, and phosphoric acid wherein said inorganic acid comprises from about 0.1% to 5% of said lotion composition.

11. The tissue paper of claim 1 wherein said antimicrobial is TRICLOSAN®.

12. The tissue paper of claim 11 wherein said antimicrobial comprises from about 0.1% to about 6% of said lotion composition.

13. The tissue paper of claim 1 wherein said hydrophilic solvent comprises from about 5% to 60% of said lotion composition.

14. The tissue paper of claim 1 wherein said skin conditioning agent is substantially free of water.

15. The tissue paper of claim 14 wherein said skin conditioning agent has a plastic or fluid consistency at 20° C.

16. The tissue paper of claim 15 wherein said skin conditioning agent is selected from the group consisting of petroleum-based skin conditioning agents; fatty acid ester skin conditioning agents; fatty alcohol skin conditioning agents; polyethylene glycols; propylene glycol; glycerin; hexylene glycol; triethylene glycol; spermaceti; squalene; cholesteryl; $C_{12}$ to $C_{50}$ waxes, $C_{12}$ to $C_{28}$ fatty acids and fatty alcohol ethers; glycerides; acetoglycerides; ethoxylated glycerides of $C_{12}$ to $C_{28}$ fatty acids; fatty esters of polyhydroxy alcohols; lanolin and lanolin derivatives; silicone polyether copolymers; dimethicones having a viscosity ranging from about 20 to 12,500 centistokes at 25° C.; amino-functional polydimethylsiloxanes having a viscosity at 20° C. of from about 5 to about 2,000 centistokes; and mixtures thereof.

17. The tissue paper of claim 16 wherein said skin conditioning agent comprises from about 0.1% to 60% of said lotion composition.

18. The tissue paper of claim 1 further comprising an immobilizing agent.

19. The tissue paper of claim 18 wherein said immobilizing agent has a melting point of at least about 25° C.

20. The tissue paper of claim 19 wherein said immobilizing agent is selected from the group consisting of $C_{12}$ to $C_{22}$ fatty alcohols; $C_{12}$ to $C_{22}$ fatty acids; sorbitan stearates; sorbitan alkylates; polyoxylated sorbitan mono-, di-, and tri-alkylates; sorbitan mono-, di-, and tri-alkylates; clays; waxes; polyhydroxy fatty acid esters; polyhydroxy fatty acid amides; and mixtures thereof.

21. The tissue paper of claim 20 wherein said immobilizing agent comprises from about 5% to 60% of said lotion composition.

22. The tissue paper of claim 1 wherein said hydrophilic surfactant has an HLB value of at least about 4.

23. The tissue paper of claim 22 wherein said hydrophilic surfactant is non-ionic.

24. The tissue paper of claim 23 wherein said hydrophilc surfactant comprises from about 0.1% to 60% of said lotion composition.

25. The tissue paper of claim 1 wherein said lotion composition further comprises other optional components selected from the group consisting of natural essential oils, vitamins, panthenol, camphor, thymol, menthol, eucalyptol, geraniol, lemon oil, methyl salicylate, clove, alcohol, and mixtures thereof.

26. The tissue paper of claim 25 wherein said other optional components comprise from about 0.1% to about 20% of said lotion composition.

27. The tissue of claim 1 wherein said lotion composition is substantially anhydrous.

28. A tissue having a lotion composition wherein said lotion composition comprises:

(A) a solid or semi-solid at 20° C.;

(B) at least one antimicrobial;

(C) at least one hydrophilic solvent;

(D) at least one skin conditioning agent; and (E) at least one hydrophilic surfactant.

* * * * *